United States Patent [19]

Fukui et al.

[11] Patent Number: 4,772,475
[45] Date of Patent: Sep. 20, 1988

[54] CONTROLLED-RELEASE MULTIPLE UNITS PHARMACEUTICAL FORMULATION

[75] Inventors: Muneo Fukui; Kouji Tomuro; Shigeru Masuyama; Atsushi Kajiyama; Tamio Hikosaka; Masayoshi Aruga; Saburo Higuchi, all of Saitama; Yoshiaki Soeishi, Tokyo, all of Japan

[73] Assignee: Yamanouchi Pharmaceutical Co., Ltd., Tokyo, Japan

[21] Appl. No.: 833,961

[22] Filed: Feb. 27, 1986

[30] Foreign Application Priority Data

Mar. 8, 1985 [JP] Japan .................................. 60-46180

[51] Int. Cl.[4] .......................... A61K 9/22; A61K 9/26; A61K 9/52
[52] U.S. Cl. .................................... 424/468; 424/469; 424/470; 424/482; 424/488
[58] Field of Search ................ 424/468, 469, 470, 488

[56] References Cited

U.S. PATENT DOCUMENTS

| 4,241,086 | 12/1980 | Iwao et al. | 514/562 |
| 4,261,970 | 4/1981 | Ogawa et al. | 424/499 |
| 4,305,958 | 12/1981 | Fujita et al. | 514/562 |
| 4,438,115 | 3/1984 | Nagano et al. | 514/255 |
| 4,469,704 | 9/1984 | Sato et al. | 514/533 |
| 4,472,398 | 9/1984 | Meszaros et al. | 514/258 |
| 4,495,189 | 1/1985 | Meszaros et al. | 514/258 |
| 4,501,752 | 2/1985 | Yokol et al. | 514/414 |
| 4,552,765 | 11/1985 | Mita et al. | 514/513 |

Primary Examiner—Shep K. Rose
Attorney, Agent, or Firm—Burgess, Ryan and Wayne

[57] ABSTRACT

A pharmaceutical controlled-release individual unit or multiple units formulation in which the individual unit comprises a granulation product obtained by adding a release controlling agent to a mixture of a physiologically active substance and units-forming substance(s) and granulating and resultant mixture, said granulation product (granules) being substantially not disintegrated but gradually releasing the physiologically active substance in the gastrointestinal tract.

5 Claims, 3 Drawing Sheets

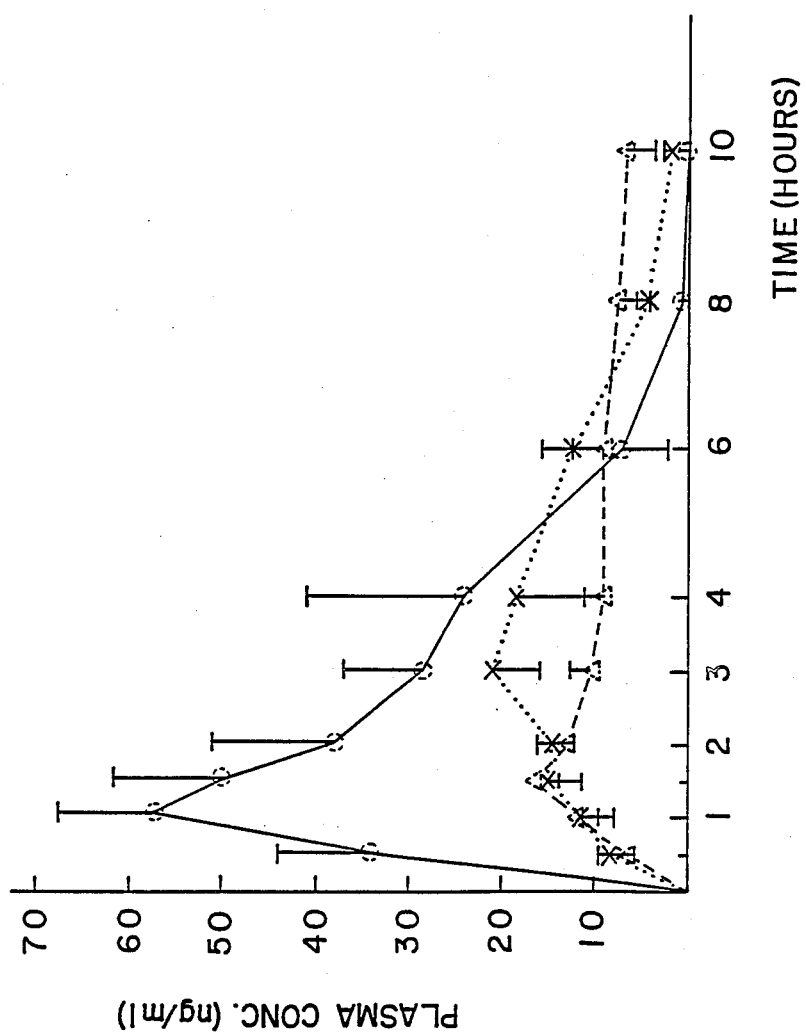

CONTROLLED-RELEASE MULTIPLE UNITS PHARMACEUTICAL FORMULATION

FIELD OF THE INVENTION

This invention relates to a novel and effective oral pharmaceutical controlled-release multiple units formulation having a high safety. More particularly, the invention relates to a pharmaceutical controlled-release individual unit or multiple units formulation in which the individual unit comprises a granulation product obtained by adding a release controlling agent to a mixture of a physiologically active substance and units-forming substance(s) and granulating the resultant mixture, said granulation product (granules) being substantially not disintegrated but gradually releasing the physiologically active substance in the gastrointestinal tract.

BACKGROUND OF THE INVENTION

When a controlled-release pharmaceutical formulation is administered to a living body, intra- or interindividual variation occurs frequently influenced by factors in the pharamceutical formulation or factors in the living body. One of the factors in the living body is a variation in a gastrointestinal transit time and as an optimum formulation for eliminating the factor, a multiple-units formulation is known (e.g., H. Bechgaad and G. H. Nielsen, Drug Devel. Ind. Pharm., 4, 53(1978)). This is a solid dosage form such as tablets, hard capsules, etc., that disintegrates in the gastrointestinal tract to form a number of units (e.g., microcapsules, microspheres, etc.,). A number of units distributes broadly in the gastrointestinal tract and an active substance is gradually released from these units.

Hitherto, there are known various materials and various production processes for obtaining an individual unit (e.g., microcapsule, microsphere, etc., ) of controlled-release multiple units pharmaceutical formulations containing an active substance.

For example, as the above-described materials, waxes, lipids, water-insoluble macromolecular materials, ion-exchange resins, etc., are known. Also, a production process of these individual units frequently requires a complicated and long step of preparing granules with an active substance and other material(s) and applying thereof enteric coating. In such a production process, there are frequently problems in the point of the production cost of products and the reproducibility of the dissolving characteristics of products.

Also, as a material forming a structure that is not easily disintegrated in the gastrointestinal tract, crystalline cellulose (the former name "microcrystalline cellulose") is known and a pharmaceutical formulation using crystalline cellulose in an amount of about 10 to 40% by weight based on the weight of the formulation is described in Japanese Patent Publication No. 5275/70. The above-metioned patent describes that the pharmaceutical formulation (the active substance of bis(o-benzoylthiamine)-disulfide) is a controlled-release one but enteric coating is necessary for further prolonging the releasing time. It is also described in the patent that the pharmaceutical formulation has a structure which does not easily disintegrate in the gastrointestinal tract, but in fact, it is known that if the amount of crystalline cellulose is about 10 to 40% by weight, the pharmaceutical formulation is insufficient in the point of strength. Furthermore, the formulation using the aforesaid amount of crystalline cellulose is also generally insufficient in the point of controlled-release of an active substance.

Furthermore, European Patent Publication No. 80341A[2] describes an invention of "oral pharmaceutical controlled release multiple-units formulation". However, in the invention, "cores" are produced by a considerably complicated process and also enteric coating is applied thereto for obtaining controlled-release thereof. Moreover, the above-described pharmaceutical formulation does not disintegrate in the stomach and is prepared with the addition of disintegrants so that the coating is eroded and the core itself disintegrates in the small intestine.

SUMMARY OF THE INVENTION

As the result of various investigations about an oral controlled-release multiple units pharmaceutical formulation which can desirably control the dissolving characteristics and shows reproducible dissolution rate without enteric coating as well as can be simply produced, the inventors have discovered that an oral pharmaceutical formulation having excellent controlled-release can be obtained by adding release controlling agent to a mixture of a physiologically active substance and units-forming substance(s) in an amount of at least 50% by weight based on the weight of the units, preparing granulation product (active substance-containing units) by a conventional method, and encapsulating the granulation product to form capsules or forming tablets of the granulation product by a conventional method.

BRIEF DESCRIPTION OF THE DRAWINGS

FIG. 3 is a graph showing the change with the passage of time of the concentration of a physiologically active substance (YM-12617) after orally administering the controlled-release multiple-units pharmaceutical formulation of this invention as capsules to beagle dogs.

DESCRIPTION OF THE PREFERRED EMBODIMENT

Figure 1:
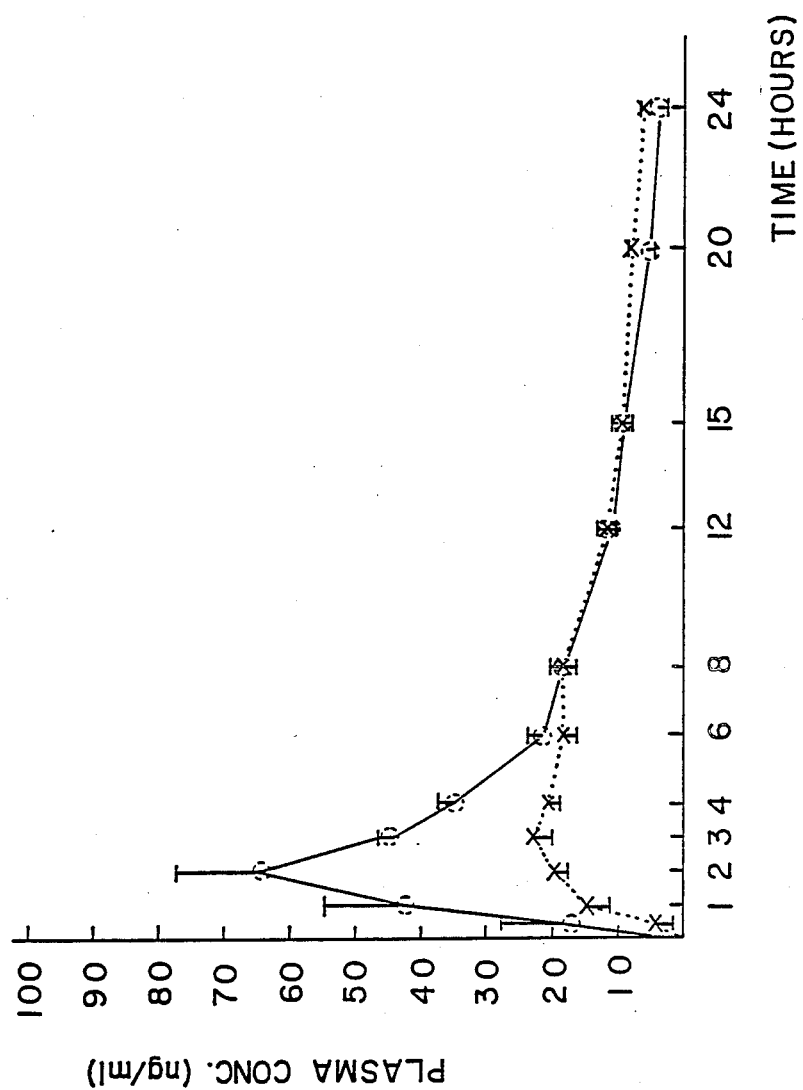
FIG. 1 and FIG. 2 are graphs each showing the change with the passage of time of the concentration of a physiologically active substance (5-[2-[2-(o-ethoxyphenoxy)ethylamino]propyl}-2-methoxybenzenesulfonamide hydrochloride: hereinafter, is referred to as YM-12617) in plasma after orally administering the controlled-release multiple units pharmaceutical formulation of this invention as tablets to humans

The above-described granulation product (active substance-containing units) for use in this invention has a property that it may be water-permeable but does not substantially disintegrate (i.e., scarecely disintegrates or does not disintegrate for at least few hours) in the gastrointestinal tract. Also, since the pharmaceutical formulation of this invention has a high physical strength, the individual unit is scarecely collapsed in the case of forming tablets under compression. Furthermore, by properly selecting the kind of an enteric coating agent and properly controlling the compounding ratio thereof at the preparation of the granulation product (active substance-containing units), the granulation product having desired dissolving characteristics can be obtained.

A suitable material as the units-forming substance for use in this invention is crystalline cellulose. Also, chitin and chitosan can be used as the units-forming substance. The amount of the units-forming substance is at least 50% by weight, preferably at least 70% by weight based on the weight of the units.

Also, as the release controlling agent in this invention, which is the concept involving binding agent for granulation, there are water-insoluble macromolecular materials, for example, acrylic acid series polymers, acrylic acid series copolymers, and cellulose derivatives such as ethyl cellulose, hydroxypropylmethyl cellulose phthalate, hydroxypropylmethyl cellulose acetate succinate, etc. The release controlling agent is suitable for use in the form of an aqueous suspension, an aqueous emulsion, or a water-containing organic solvent solution. They are also commercially available as, for example, Eudragit L 30 D (Röhm Co., trade name; aqueous suspension of a methacrylic acid-ethyl acrylate copolymer), Eudragit E 30 D (aqueous suspension of an ethyl acrylate-methyl methacrylate copolymer), Aquacoat ECD-30 (aqueous suspension of ethyl cellulose), etc. They can be used as the release controlling agent as they are or in a state of being diluted with water. Also, low-substituted hydroxypropyl cellulose (L-HPC) or aforesaid ethyl cellulose can be used as an aqueous gel. Furthermore, these water-insoluble polymers may be also used as solution systems in a water-base mixed solvent containing an organic solvent.

In addition, water itself can be used as the release controlling agent. That is, crystalline cellulose can be formed into a granulation product by the addition of water.

There is no particular restriction about the amount of the release controlling agent but the amount suitable for wet granulation may be used. There is also no particular restriction about the concentration of the release controlling agent (as an aqueous liquid material) but since if the compounding ratio of the water-insoluble polymer is high, the release of the physiologically active substance is delayed, the amount of the release controlling agent (as aqueous liquid material) used may be suitably selected. Although there is no particular restriction about the amount of the release controlling agent, general standard is 0–30% (as solid component) or 50–150% (as aqueous liquid material, or water) by weight based on the weight of the units. In addition, a water-soluble polymer which is usually used as a binder, such as hydroxypropyl cellulose, polyvinyl pyrrolidone, etc., may be used as the release controlling agent.

In this invention, for controlling the dissolving characteristics of an active substance, an alkaline earth metal salt (or an alkaline metal salt) of a higher fatty acid or an enterosoluble polymer may be added in the case of producing the granulation product (active substance-contaning units). The addition of the aforesaid material is effective when the physiologically active substance is a so-called micromedicament. Examples of the alkaline earth metal salt or alkaline metal salt of a higher fatty acid are magnesium stearate, calcium stearate, etc. Also, examples of the enterosoluble polymers are cellulose acetate phthalate, hydroxypropylmethyl cellulose phthalate, a methacrylic acidmethyl methacrylate copolymer (Eudragit L, S), etc. The compounding amount thereof is usually 1 to 15% by weight.

When such enterosoluble polymer is used, PEG 6000, Tween 80 (trade name), triacetin, etc. may be added as plasticizer. The compounding amount thereof is usually 0 to 15% by weight based on the weight of the release controlling agent (solid component). In addition, an alkaline metal halide or an alkaline earth metal halide, such as sodium chloride, calcium chloride, etc., can be used for the same purpose.

As described above, the release of the physiologically active substance can be controlled by selecting the kind of the release controlling agent and/or controlling the compounding amount of the alkaline earth metal salt (or alkaline metal salt) of a higher fatty acid or an enterosoluble polymer but according to the characteristics of the active substance, the release thereof can be also delayed by subjecting the active substance itself to a hydrophobic treatment. The hydrophobic treatment can be performed by microcapsulating the active substance by, for example, spray congealing method using wax, etc. Examples of the wax which is used for the purpose are hydrogenated vegetable oils usch as hydrogenated castor oil, etc.

There is no particular restriction about the physiologically active substance for use in this invention. Also the amount of the active substance is generally less than 30% by weight based on the weight of the units.

In the test examples and examples described hereinbelow, 5-{2-[2-(o- ethoxyphenoxy)ethylamino]propyl}-2-methoxybenzenesulfonamide hydrochloride (YM-12617) having a relatively low solubility in water (about 0.3 to 0.5%) was used as the active substance but active substance having a high solubility can be, as a matter of course, used in this invention.

YM-12617 shows an α-blocking action and can be used for the treatments of hyperpiesia, cardiac insufficiency, lower urinary desease, etc.

The individual controlled-release unit of this invention is composed of a physiologically active substance, units-forming substance(s), and, if necessary, an alkaline earth metal salt (or an alkaline metal salt) of a higher fatty acid or an enterosoluble polymer. In this case, according to the purposes, usual additives such as a filler, a coloring agent, etc., can be added thereto.

The mixture thus obtained is granulated after the addition of the above-described aqueous liquid material or water as a release controlling agent. The granulation is performed by an agitation type apparatus, a rotation type apparatus, a centrifugal type apparatus, a fluidized bed type apparatus, or the like.

The size (diameter) of the granulation product (particles) is 0.1 to 1.5 mm, preferably 0.2 to 1.0 mm.

The individual active-substance-containing units thus obtained are formed into a multiple-units formulation such as tablets, capsules, granules, etc.

EFFECTS OF THE INVENTION

The active substance-containing units of this invention have a high mechanical strength, keep most of their form without being disintegrated even in the case of forming tablets using the units, and are separated into individual unit and widely dispersed in the gastrointestinal tract when they are administered to a living body. Also, the pharmaceutical units are water-permeable but do not substantially disintegrate and gradually release the active substance in the gastrointestinal tract, whereby a long controlled release can be attained. Also, a intra- and inter-subject variation are very small and are excellent in reproducibility. Furthermore, the pharmaceutical formulation of this invention can be obtained by a simple and safety production process.

Then, the test method and results of dissolution characteristics and concentrations in plasma of the active substance of the controlled-release formulation of this invention are shown below.

(1) Dissolution Test

§Test Procedure

The test was performed by the paddle method of the 2nd dissolution test method in the Japan Pharmacopoeia. That is, the test was performed by a UV method or a liquid chromatograph method shown below at a rotation speed of the paddle of 150 r.p.m., using 500 ml of a 1st liquid (artificial gastric juice) of the Japanese Pharmacopoeia and 500 ml of a 2nd liquid (artificial intestinal juice) in the Japanese Pharmacopoeia, respectively. A sample was first tested in the 1st liquid for one hour followed by the test in the 2nd liquid for one hour.

(i) UV Method

The pharmaceutical formulation obtained in each example shown below was used as a sample. The amount of each sample corresponding to 50 mg of YM-12617 was subjected to the aforesaid disolution test, the dissolved liquid was filtered, and the active substance in the filtrate was determined at a detection wavelength of 278 nm.

(ii) High Performance Liquid Chromatograph Method (HPLC Method)

The pharmaceutical formulation prepared in each example was used as a sample. The amount of the sample corresponding to 1 mg of YM-12617 was subjected to the aforesaid dissolution test, the dissolved liquid was filtered, and the active substance was determined by the following operation conditions.

Operation Conditions:
  Detector: Ultraviolet Spectrophotometer (Detection wavelength of 225 nm)
  Column: In a stainless tube of about 4 mm in inside diameter and about 150 mm in length was packed about 5 μm of octadecylsililated silica gel (e.g., Nucleosil 5C18, trade name) as a packing agent
  Column Temperature: About 35° C.
  Mobile Phase: Mixture of 0.05N perchloric acid and acetonitrile (7:3).
  Flow rate: Constant amount of 0.8 to 1.5 ml per minute.

§Test Results

The results thus obtained are shown in Table 1.

TABLE 1

| Example No. | % of YM-12617 in the units (w/w) | Test Method | 1st Liquid* (1 hour) | 2nd Liquid* (1 hour) | Note |
|---|---|---|---|---|---|
| 1 | 1 | UV | 49.6 | | (A)** |
| 20 | " | HPLC | 50.3 | 57,6 | " |
| 4 | " | UV | 45.6 | | " |
| 5 | 0.5 | UV | 52.4 | 66.2 | " |
| 24 | " | HPLC | 60.4 | 72.6 | " |
| 6 | " | UV | 54.6 | | " |
| 8 | 1 | UV | 42.7 | | (B)** |
| 9 | " | " | 29.2 | | " |
| 10 | " | " | 32.5 | | " |
| 11 | 0.5 | " | 30.9 | | " |
| 12 | 5 | UV | 42.7 | | (C)** |
| 13 | " | " | 16.2 | 41.7 | " |
| 23 | " | " | 19.0 | 61.0 | " |
| 14 | 2 | UV | 54.2 | | (D)** |
| 15 | 5 | " | 37.5 | 90.6 | " |
| 22 | " | HPLC | 38.0 | 91.0 | " |
| 16 | " | UV | 40.9 | 94.6 | " |
| 19 | 1 | " | 36.8 | 44.8 | " |
| 21 | " | HPLC | 41.3 | 44.2 | " |

*By the Japan Pharmacopoeia
**(A): Eudragit L30D-55 was used as the release controlling agent
(B): Particles containing magnesium stearate. The release controlling agent was same as (A).
(C): Granules containing ethyl cellulose as the release controlling agent
(D): Water was used as the release controlling agent (2) Absorption Studies following Oral Administration (A)

(i) The tablet obtained in Example 20 was used as the sample of this invention and conventional tablet obtained in Refence Example 1 was used as a control. The amount of each sample corresponding to 1 mg of YM-12617 was orally administered to five adult male subjects, respectively, by a cross over method. Then, blood samples were withdrawn at definite time intervals and the concentration of the active substance in plasma was measured by the method shown below.

(ii) Determination Method of YM-12617 in Plasma:

After adding 0.5 ml of an aqueous solution of internal standard substance (containing 0.5 μg of amosulalol hydrochloride) to 1.5 ml of plasma, 1 ml of a saturated aqueous solution of sodium hydrogencarbonate was added thereto and the active substance was extracted with 4 ml of ehtyl acetate. The ethyl acetate extract was further extracted with 2.5 ml of 0.4N hydrochloric acid. The hydrochloric acid layer thus obtained was adjusted to weak alkaline by the addition of 2 ml of a saturated aqueous solution of sodium hydrogencarbonate and then re-extracted with 4 ml of ethyl acetate. The ethyl acetate layer thus obtained was distilled under reduced pressure and after adding 0.05 ml of an aqueous solution of 0.1M sodium hydrogencarbonate and 0.1 ml of an acetone solution of 500 μg of dansyl chloride, the reaction was performed for 120 minutes at 35° C. After adding 4 ml of ether to the reaction mixture, the organic layer thus formed was washed with 5 ml of water and then with 5 ml of an aqueous solution of 0.2N hydrohcloric acid. The solvent was distilled off from the organic layer, the residue thus formed was dissolved in 0.05 ml of the mixed liquid for the mobile phase of the following operation condition, and using all of the solution the active substance was determined by a liquid chromatography under the following operation condition.

The retension times for dansyl-YM-12617 and dansyl-amosulalol when the flow rate of the eluent was 1.4 ml/min. were 8.1 minutes and 12.5 minutes, respectively.

Operation Condition
  Detector: Fluorescent Photometer (Excitation wavelength 365 nm, fluorescent wavelength 500 nm)
  Coulmn: In a stainless tube of about 4 mm in inside dimater and about 250 mm in length was packed by about 5 μm of silica gel (e.g., Lichrosorb SI 100, trade name, made by Merck & Co., Ltd.) as a filler.
  Column Temperature: About 10° C.
  Mobile Phase: Mixture of benzene and methanol (100:1).

Flow Rate: Constant flow rate of 1.2 to 1.9 ml per minute.

(iii) The results thus obtained are shown in Table 2, Table 3, and FIG. 1.

In FIG. 1, "———○" shows ordinary tablet obtained in Reference Example 1, and "○---✗" shows tablet obtained in Example 20.

(B)

(i) The tablet obtained in Example 21 was used as a sample of this invention and an conventional tablet obtained in Reference Example 1 was used as a control. The amount of each sample corresponding to 1 mg of YM-12617 was orally administered to five adult male subjects, respectively, by a cross over method, the

TABLE 2

Concentration of unchanged YM-12617 in plasma when the tablet of Example 20 was orally administered to humans in an amount corresponding to 1 mg as YM-12617 (unit ng/ml)

| Subject | Time | | | | | | | | | | | AUC |
| | 0.5 | 1.0 | 2.0 | 3.0 | 4.0 | 6.0 | 8.0 | 12.0 | 15.0 | 20.0 | 24.0 | (ng · hr/ml) |
| --- | --- | --- | --- | --- | --- | --- | --- | --- | --- | --- | --- | --- |
| N | 9.9 | 17.0 | 21.0 | 24.1 | 18.6 | 15.3 | 16.2 | 12.9 | 8.1 | 7.7 | 6.3 | 292.6 |
| K | 11.4 | 25.8 | 18.4 | 30.0 | 25.5 | 25.0 | 24.2 | 16.4 | 15.3 | 10.1 | 8.7 | 415.8 |
| T | N.D. | 17.5 | 17.5 | 14.7 | 18.4 | 15.1 | 17.1 | 10.5 | 8.1 | 7.8 | 5.8 | 270.3 |
| F | N.D. | 5.3 | 26.0 | 27.7 | 23.7 | 15.4 | 20.4 | 10.7 | 7.5 | 5.7 | 3.7 | 285.7 |
| S | N.D. | 8.6 | 14.9 | 18.1 | 16.4 | 20.3 | 13.1 | 8.3 | 8.2 | 7.5 | 5.4 | 250.4 |
| Mean Value | 4.3 | 14.8 | 19.6 | 12.9 | 20.5 | 18.2 | 18.2 | 11.6 | 9.4 | 7.8 | 6.0 | 302.9 |
| S.E. | 2.6 | 3.6 | 1.9 | 2.9 | 1.7 | 2.0 | 1.9 | 1.3 | 1.5 | 0.7 | 0.8 | 29.1 |

N.D.: Not detected;
S.E.: Standard error

TABLE 3

Concentration of unchanged YM-12617 in plasma when the conventional tablet of Reference example 1 was orally administered to humans in an amount corresponding to 1 mg as YM-12617 (unit ng/ml)

| Subject | Time | | | | | | | | | | | AUC |
| | 0.5 | 1.0 | 2.0 | 3.0 | 4.0 | 6.0 | 8.0 | 12.0 | 15.0 | 20.0 | 24.0 | (ng · hr/ml) |
| --- | --- | --- | --- | --- | --- | --- | --- | --- | --- | --- | --- | --- |
| N | 21.6 | 64.7 | 66.8 | 47.1 | 39.5 | 21.9 | 14.6 | 11.5 | 9.2 | 7.4 | 4.5 | 439.4 |
| K | 56.5 | 78.6 | 112.3 | 50.4 | 41.8 | 27.4 | 25.1 | 11.7 | 14.1 | 5.5 | 3.9 | 572.6 |
| T | 7.6 | 29.9 | 56.1 | 41.9 | 33.7 | 13.2 | 17.4 | 9.8 | 7.0 | 3.7 | 1.9 | 336.1 |
| F | N.D. | 24.4 | 47.2 | 42.8 | 28.7 | 21.7 | 15.1 | 10.4 | 6.3 | 5.5 | 2.4 | 331.2 |
| S | N.D. | 15.1 | 41.2 | 43.0 | 31.5 | 23.1 | 20.0 | 12.1 | 9.3 | 4.9 | 6.0 | 362.6 |
| Mean Value | 17.1 | 42.5 | 64.7 | 45.0 | 35.0 | 21.5 | 18.4 | 11.1 | 9.2 | 5.4 | 3.7 | 408.4 |
| S.E. | 10.6 | 12.3 | 12.7 | 1.6 | 2.5 | 2.3 | 1.9 | 0.4 | 1.4 | 0.6 | 0.7 | 45.4 |

As is clear from FIG. 1, in the case of administering the tablets prepared in Example 20, the concentration pattern of the active substance in plasma was good and showed the following features.

(a) The ratio of Cmax/Cmin is small, which shows long acting characteristics.

(b) Intra-individual variation is small.

blood was withdrawn at definite time intervals, and the concentration of the active substance in plasma was measured by the aforesaid method (A) (ii).

Figure 2:
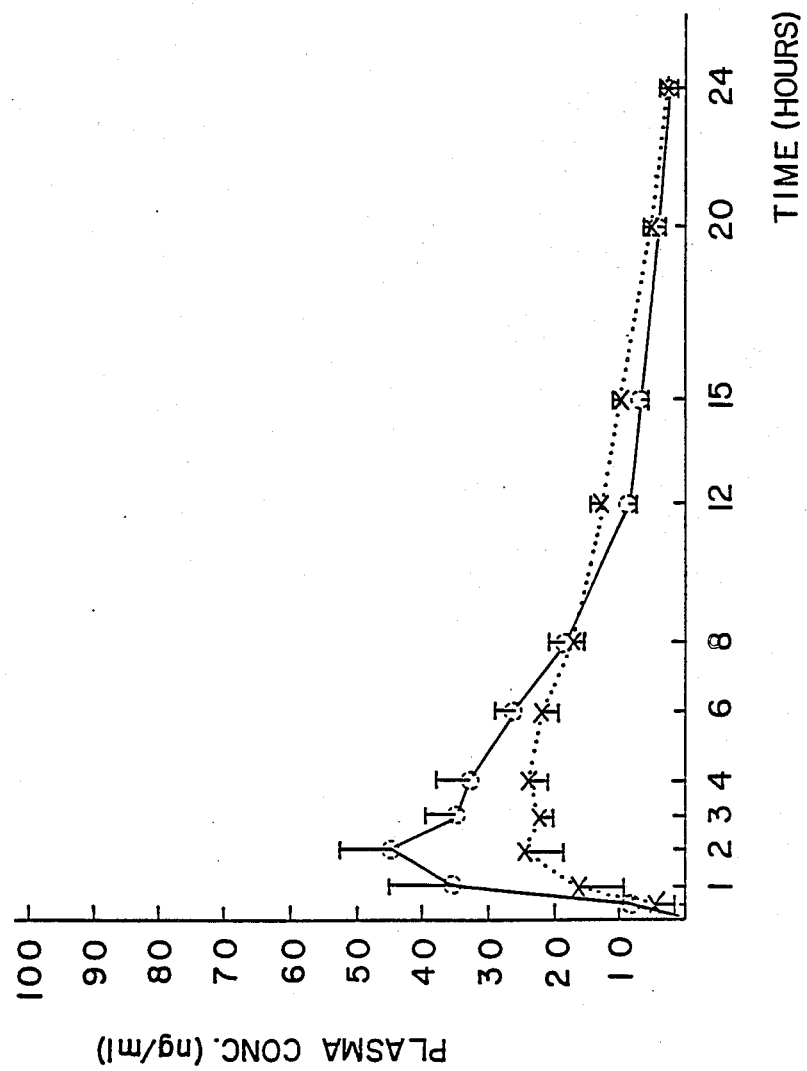

(ii) The results thus obtained are shown in Table 4, Table 5, and FIG. 2.

In FIG. 2, "———○" shows ordinary tablet obtained in Reference Example 1, and "○---✗" shows tablet obtained in Example 21.

TABLE 4

Concentration of unchanged YM-12617 in plasma when the tablet of Example 21 was orally administered to humans in an amount corresponding to 1 mg as YM-12617 (unit ng/ml)

| Subject | Time | | | | | | | | | | | AUC |
| | 0.5 | 1.0 | 2.0 | 3.0 | 4.0 | 6.0 | 8.0 | 12.0 | 15.0 | 20.0 | 24.0 | (ng · hr/ml) |
| --- | --- | --- | --- | --- | --- | --- | --- | --- | --- | --- | --- | --- |
| M | N.D. | 2.7 | 16.7 | 21.5 | 22.1 | 25.5 | 21.0 | 8.5 | 9.0 | 4.8 | 3.4 | 281.5 |
| K | 8.7 | 38.1 | 36.2 | 25.7 | 32.6 | 20.0 | 17.3 | 11.6 | 12.4 | 4.6 | 4.4 | 355.3 |
| MI | N.D. | N.D. | 5.8 | 15.3 | 28.6 | 22.3 | 17.4 | 13.4 | 10.1 | 8.9 | 5.6 | 299.4 |
| N | 14.4 | 23.4 | 34.4 | 21.1 | 16.6 | 13.4 | 10.9 | 9.3 | 6.0 | 2.6 | N.D. | 232.9 |
| KA | N.D. | 17.8 | 29.4 | 27.8 | 19.4 | 27.8 | 18.5 | 18.7 | 10.8 | 5.1 | 1.5 | 345.4 |
| Mean Value | 4.6 | 16.4 | 24.5 | 22.3 | 23.9 | 21.8 | 17.0 | 12.3 | 9.7 | 5.2 | 3.0 | 302.9 |
| S.E. | 3.0 | 7.0 | 5.8 | 2.2 | 3.0 | 2.5 | 1.7 | 1.8 | 1.1 | 1.0 | 1.0 | 22.3 |

TABLE 5

Concentration of unchanged YM-12617 in plasma when the conventional tablet of Reference example 1 was orally administered to humans in an amount corresponding to 1 mg as YM-12617 (unit ng/ml)

| Subject | Time | | | | | | | | | | | AUC |
| | 0.5 | 1.0 | 2.0 | 3.0 | 4.0 | 6.0 | 8.0 | 12.0 | 15.0 | 20.0 | 24.0 | (ng · hr/ml) |
| --- | --- | --- | --- | --- | --- | --- | --- | --- | --- | --- | --- | --- |
| M | 17.0 | 44.7 | 34.4 | 21.9 | 18.8 | 18.2 | 11.8 | 6.3 | 3.2 | 3.2 | 2.4 | 252.4 |
| K | 6.3 | 47.9 | 64.9 | 34.3 | 37.2 | 28.2 | 12.6 | 8.7 | 6.5 | 3.0 | N.D. | 358.2 |

TABLE 5-continued

Concentration of unchanged YM-12617 in plasma when the conventional tablet of Reference example 1 was orally administered to humans in an amount corresponding to 1 mg as YM-12617 (unit ng/ml)

| Subject | Time | | | | | | | | | | | AUC |
|---|---|---|---|---|---|---|---|---|---|---|---|---|
| | 0.5 | 1.0 | 2.0 | 3.0 | 4.0 | 6.0 | 8.0 | 12.0 | 15.0 | 20.0 | 24.0 | (ng · hr/ml) |
| MI | N.D. | N.D. | 20.4 | 26.8 | 23.7 | 20.8 | 21.6 | 7.8 | 6.0 | 3.0 | 1.6 | 257.2 |
| N | 15.1 | 51.5 | 54.8 | 45.5 | 48.7 | 35.1 | 18.0 | 8.2 | 9.9 | 4.5 | 3.3 | 438.9 |
| KA | 2.8 | 33.6 | 49.4 | 45.1 | 35.1 | 27.8 | 26.1 | 10.4 | 7.4 | 6.4 | 5.1 | 412.7 |
| Mean Value | 8.2 | 35.5 | 44.8 | 34.7 | 32.7 | 26.0 | 18.0 | 8.3 | 6.6 | 4.0 | 2.5 | 343.9 |
| S.E. | 3.4 | 9.4 | 7.8 | 4.7 | 5.3 | 3.0 | 2.7 | 0.7 | 1.1 | 0.7 | 0.9 | 38.6 |

As is clear from FIG. 2, in the case of administrating the tablet prepared in Example 21, the concentration pattern of the active substance in plasma was good and showed the following features.

(a) The ratio of Cmax/Cmin is small, which shows long acting characteristics.

(b) Inter-individual variation is small.

(C)

(i) The tablet obtained in Example 22 and the capsule obtained in Example 23 were used as the samples of this invention and conventional tablet obtained in Reference Example 2 was used as a control. The amount of each sample corresponding to 10 mg of YM-12617 was orally administered to six beagle dogs by a cross over method, the blood was withdrawn at definite intervals, and the concentration of the active substance in plasma was measured by the aforesaid method (A) (ii).

(ii) The results are shown in FIG. 3.

In FIG. 3, "———" shows ordinary tablet obtained in Reference Example 2, "— — —X" shows tablet obtained in Example 22, and "— — —△" shows capsule obtained in Example 23.

As is clear from FIG. 3, in the case of administering the tablet prepared in Example 22 and the capsule prepared in Example 23, the concentration patterns of the active substance in plasma are good and show the following features.

(a) The ratio of Cmax/Cmin is small.

(b) Inter-individual variation is small.

(3) Mechanical Strength of Active Substance-Containing Units (Particles)

Using the particules prepared by the same manner as Example 15, tablets were produced by the following formula changing the compression pressure at tabletmaking and thereafter dissolution rate of the active substance was measured. (The determination was made by HPLC method). The results thus obtained are shown in Table 6.

| Tablet Formula: | |
|---|---|
| Particles | 4.0 mg |
| Lactose | 62.0 mg |
| Corn Starch | 28.5 mg |
| CMC-Ca | 5.0 mg |
| Magnesium Stearate | 0.5 mg |
| Total | 100 mg |

TABLE 6

| Compression Pressure | % Dissolved JP, 1st Liquid* | |
|---|---|---|
| | (1 hour) | (2 hours) |
| 2261 kg/cm² oil pressure-press | 45.9 | 57.6 |

TABLE 6-continued

| Compression Pressure | % Dissolved JP, 1st Liquid* | |
|---|---|---|
| | (1 hour) | (2 hours) |
| 4522 kg/cm² oil pressure-press | 45.9 | 56.4 |
| 2261 kg/cm² (Single press) | 46.6 | 62.6 |
| Particles | 41.7 | 57.1 |

As is clear from the above results, there is almost no change of dissolution characteristics by the change of tabletting pressure. That is, it can be seen that the formulation of this invention can sufficiently endure (individual particle is not collapsed) to the tabletting pressure as described above and keeps a constant dissolution characteristics.

(4) Relationship between dissolution characteristics and rotation speed in dissolution tests The rotation speed of the paddle in the dissolution test (1) described above was changed and the influence of the rotation speed on the dissolution rate was studied. (The active substance was determined by UV method.). The results thus obtained are shown in Table 7.

TABLE 7

| Example No. | % dissolved, JP, 1st Liquid*, After 1 Hour. Rotation speed of the Paddle | | | |
|---|---|---|---|---|
| | 50 rpm | 100 rpm | 150 rpm | 200 rpm |
| 1 | 42.1 | 45.7 | 45.4 | 45.3 |
| 19 | 36.0 | 36.3 | 36.4 | 39.6 |

As is clear from Table 7, it can be seen that there is no change of the dissolution characteristics by the change of the rotation speed, which shows the formulation of this invention is scarcely influenced by the factor (the motion of the gastrointestinal tract) in the living body side.

(5) Stability of Dissolution Characteristics with the Passage of Time

The product obtained in each example was stored under severe conditions shown in Table 8 below for one month and then the dissolution test as in above-described test (1) was performed on the product. In this case, the determination of the active substance was performed by UV method.

The results thus obtained are shown in Table 8.

TABLE 8

| Test No. (Example No.) | Dissolution Rate (%) | | |
|---|---|---|---|
| | Initial (%) | Value After 1 Month | |
| | | 50° C., Closed | 40° C., 75% RH |
| 4 | 45.6 | 45.5 | — |
| 11 | 32.9 | 37.1 | 34.2 |

TABLE 8-continued

| Test No. (Example No.) | Dissolution Rate (%) | | |
|---|---|---|---|
| | Initial (%) | Value After 1 Month | |
| | | 50° C., Closed | 40° C., 75% RH |
| 12 | 42.0 | 43.8 | 42.7 |
| 15 | 39.5 | 37.5 | 29.6 |
| 16 | 38.7 | 36.9 | 30.8 |
| 23 | 18.4 | 21.7 | 19.2 |

As is clear from the above results, it can be seen when the samples of this invention are stored under the severe conditions, the change in the dissolution characteristics is very small and thus, the formulations are stable with the passage of time.

(6) Good Dissolution Reproducibility

Three samples were prepared by the same manner as in Example 4 and the dissolution test as above was performed on each sample (the dtermination of the active substance was performed by UV method). The results thus obtained are shown in Table 9.

TABLE 9

| Sample No. (Example No.) | % dissolved JP, 1st Liquid* (1 hour) |
|---|---|
| Example 4 | 45.6 |
| 4 - 1 | 45.4 |
| 4 - 2 | 45.9 |
| 4 - 3 | 45.3 |

*The 1st liquid in Tables 6, 7, and 9 above is artificial gastric juice in the Japan Pharmacopoeia.

From the results shown in Table 9, it can be seen that the samples of this invention show good dissolution reproducibility.

Then, the invention will be described below more practically.

EXAMPLE 1

(Production of active substance-containing units)

After sufficiently mixing 5 g of YM-12617 and 470 g of crystalline cellulose, a mixture of 83.3 g (25 g as solid component) of Eudragit L30D-55(Röhm Co.) and 500 g of water was added to the aforesaid mixture and the resultant mixture was granulated by a high-speed mixer. The granules obtained were spheres having particle sizes of 0.1 to 1.5 mm, mainly 0.2 to 1.0 mm.

EXAMPLES 2 to 7

By following the same procedure as Example 1 using the formulas shown in Table 10 below, active substance-containing units were prepared.

TABLE 10

| Formula (g) | Example No. | | | | | |
|---|---|---|---|---|---|---|
| | 2 | 3 | 4 | 5 | 6* | 7 |
| YM-12617 | 5 | 5 | 5 | 2.5 | 2.5 | 1.25 |
| Crystalline Cellulose | 445 | 395 | 482.5 | 472.5 | 472.5 | 473.75 |
| Eudragit L30D-55 (Solid comp.) | 166.6 (50) | 333.3 (100) | 41.7 (12.5) | 83.3 (25) | 83.3 (25) | 83.3 (25) |

*Centrifugal fluidized bed granulator was used.

EXAMPLE 8

After sufficiently mixing 5 g of YM-12617, 420 g of crystalline cellulose, and 50 g of magnesium stearate, a mixture of 83.3 g (25 g as solid component) of Eudragit L30D-55 and 500 g of water was added to the aforesaid mixture and the resultant mixture was kneaded and granulated by a centrifugal fluidized bed granulator. The granules obtained were spheres having particle sizes of 0.1 to 1.5 mm, mainly 0.2 to 1.0 mm.

EXAMPLES 9 to 11

By following the same procedure as Example 8 using the formulas shown in Table 11, active substance-containing units were prepared.

TABLE 11

| Formula (g) | Example No | | |
|---|---|---|---|
| | 9 | 10 | 11 |
| YM-12617 | 5 | 5 | 2.5 |
| Crystalline Cellulose | 460 | 445 | 462.5 |
| Magnesium Stearate | 10 | 25 | 10 |
| Eudragit L30D-55 (Solid component) | 83.3 (25) | 83.3 (25) | 83.3 (25) |

EXAMPLE 12

After sufficiently mixing 20 g of YM-12617, 300 g of crystalline cellulose, and 80 g of ethyl cellulose, 230 g of a mixed solvent of ethanol and water of 8:2 in mixing ratio was added to the mixture and the resultant mixture was granualted by a high-speed mixer. The particle size, etc., of the particles thus obtained were same as described above.

EXAMPLE 13

By following the same procedure as Example 12 granulating the mixture by means of an ultra high-speed mixer, granules were prepared. The particle size, etc., of the granules were same as above.

EXAMPLE 14

After sufficiently mixing 5 g of YM-12617 and 495 g of crystalline cellulose, 500 g of water was added to the mixture and the resultant mixture was granulated by a high-speed mixer. The particle size, etc., of the granules thus obtained were same as above.

EXAMPLE 15 to 18

By following the same procedure as Example 14 using the formulas shown in Table 12 below, active substance-containing units were prepared.

TABLE 12

| Formula (g) | Example No. | | | |
|---|---|---|---|---|
| | 15 | 16 | 17 | 18 |
| YM-12617 | 25 | 25 | 2.5 | 1.25 |
| Crystalline Cellulose | 475 | 475* | 497.5 | 498.75 |

*Centrifugal fluidized bed granulator was used.

EXAMPLE 19

After melting 80 g of hydrogenated castor oil, 10 g of YM-12617 and 30 g of low-substituted hydroxypropyl cellulose were dispersed in the melt and the resultant mixture was granulated by a spray congealing method. After sufficiently mixing 60 g (5 g as YM-12617) of the granulated product thus obtained and 440 g of crystalline cellulose, 500 g of water was added to the mixture and the resultant mixture was granulated by means of a centrifugal fluidized bed granulator. The particle size, etc., of the granules thus obtained were same as above.

EXAMPLE 20

(manufacturing of multiple units pharmaceutical formulation)

To 20 g of the particles (active substance-containing units) obtained in Example 1 were added 44.9 g of lactose, 20 g of starch, 9.7 g of crystalline cellulose, 5 g of CMC-Ca, and 0.5 g of magnesium stearate and tablets were prepared using the mixture thus obtained by a conventional method (one tablet of 100.1 mg contained 0.2 mg of YM-12617).

EXAMPLES 21 to 23

By following the same procedure as Example 20 using the formulas shown in Table 13 below, multiple units pharmaceutical formulations were prepared.

TABLE 13

| Formula, etc. | Example No. | | |
|---|---|---|---|
| | 21 | 22 | 23 |
| Granules (Active Substance-Containing Units) | 20 g* | 50 g** | 50 g*** |
| Lactose | 46.5 g | 64.9 g | 50 g |
| Starch | 28 g | — | — |
| Magnesium Stearate | 0.5 g | — | — |
| Crystalline Cellulose | — | 70 | — |
| CMC-Ca | — | 10 | — |
| Hydrogenated Oil | — | 5 | — |
| Formulation | Tablet | Tablet | Capsule[4*] |
| Weight of one formulation | 100 mg | 200 mg | 100 mg |

*The granules obtained in Example 19
**The granules obtained in Example 15
***The granules obtained in Example 13
[4*]Capsulated by a conventional method.

EXAMPLE 24

After sufficiently mixing 40 g of the granules obtained in Example 5, 24 g of lactose, 34.54 g of crystalline cellulose, 12 g of low-substituted hydroxypropyl cellulose, and 3 g of corn starch, 40 g of 10% corn starch paste was added to the mixture and the resultant mixture was granulated by a conventional method. Then, 2.4 g of a hydrogenated oil and 0.06 g of calcium stearate were added to the granules thus obtained and tablets were manufactured using the resultant mixture by a conventional method (one tablet of 120 mg contained 0.2 mg of YM-12617).

EXAMPLE 25

After sufficiently mixing 5 g of YM-12617 and 467.5 g of crystalline cellulose, a mixture obtained by adding 414.2 g of water and 2.5 g of PEG 6000 to 83.3 g (25 g as solid component) of Eudragit L30D-55 (trade name) was added to the aforesaid mixture and the resulted mixture was granulated by a high-speed mixer. The granules were spheres having particle sizes of 0.1 to 1.5 mm, mainly 0.2 to 1.0 mm.

REFERENCE EXAMPLES 1 and 2

Conventional tablets were prepared using the formulas shown in Table 14 below.

TABLE 14

| Formula | Reference Example No. | |
|---|---|---|
| | 1 | 2* |
| YM-12617 | 0.2 g | 2.5 g |
| Lactose | 66.7 g | 63.0 g |
| Starch | 28.6 g | — |
| Starch (for paste) | 3.5 g | — |
| Magnesium Stearate | 1.0 g | 1.0 g |
| Corn Starch | — | 30.0 g |
| Corn Starch (for paste) | — | 3.5 g |
| tablet | 100 mg | 100 mg |

*Prepared by fluidized bed granulator.

What is claimed is:

1. A pharmaceutical controlled-release individual unit or multiple unit formulation in which said individual unit consists essentially a granulation product obtained by adding a release controlling agent selected from the group consisting of acrylic acid polymers, acrylic acid copolymers and mixtures thereof with cellulose derivatives, to a mixture of physiologically active substances and crystalline cellulose, in an amount such that at least 50% by weight based on the weight of the units is said crystalline cellulose and granulating the resultant mixture and wherein said granulation product does not substantially disintegrate but gradually releases the physiologically active substance in the gastrointestinal tract.

2. The pharmaceutical formulation as claimed in claim 1, wherein the release controlling agent is a methacrylic acid-ethyl acrylate copolymer or mixtures of said copolymer and ethyl cellulose.

3. The pharmaceutical formulation as claimed in claim 1, wherein the release controlling agent further contains water.

4. The pharmaceutical formulation as claimed in claim 1, 2, or 3, wherein the physiologically active substance is 5-{2-[2-(o-ethoxypheoxy)ethylamino]-propyl}-2-methoxybenzenesulfonamide hydrochloride (YM-12617).

5. The pharmaceutical formulation as claimed in claim 1, 2, 3, or 4, wherein the individual unit is granulation product having diameter of 0.1 to 1.5 mm.

* * * * *

UNITED STATES PATENT AND TRADEMARK OFFICE
CERTIFICATE OF CORRECTION

PATENT NO. : 4,772,475

DATED : September 20, 1988

INVENTOR(S) : Fukui et al.

It is certified that error appears in the above-identified patent and that said Letters Patent is hereby corrected as shown below:

Col. 2, line 36: change "(5-{2-[2-" to --5-{2-[2- --

Signed and Sealed this

Nineteenth Day of December, 1989

Attest:

JEFFREY M. SAMUELS

*Attesting Officer*    *Acting Commissioner of Patents and Trademarks*